United States Patent
Hupfeld et al.

(10) Patent No.: US 10,960,016 B2
(45) Date of Patent: *Mar. 30, 2021

(54) CAPSULES CONTAINING HIGH DOSES OF KRILL PHOSPHOLIPIDS

(71) Applicant: Aker BioMarine Antarctic AS, Stamsund (NO)

(72) Inventors: Stefan Hupfeld, Oslo (NO); Tove Jule Evjen, Oslo (NO); Finn Myhren, Oslo (NO); Håvard Thøgersen, Oslo (NO)

(73) Assignee: Aker BioMarine Antarctic AS, Stamsund (NO)

( * ) Notice: Subject to any disclaimer, the term of this patent is extended or adjusted under 35 U.S.C. 154(b) by 288 days.

This patent is subject to a terminal disclaimer.

(21) Appl. No.: 15/118,343

(22) PCT Filed: Feb. 12, 2015

(86) PCT No.: PCT/EP2015/053024
§ 371 (c)(1),
(2) Date: Aug. 11, 2016

(87) PCT Pub. No.: WO2015/121381
PCT Pub. Date: Aug. 20, 2015

(65) Prior Publication Data
US 2017/0182073 A1    Jun. 29, 2017

(30) Foreign Application Priority Data
Feb. 12, 2014 (GB) .................................. 1402457

(51) Int. Cl.
| | | |
|---|---|---|
| *A61K 31/685* | (2006.01) | |
| *A61K 35/612* | (2015.01) | |
| *A23L 33/12* | (2016.01) | |
| *A23L 33/115* | (2016.01) | |
| *A23L 33/10* | (2016.01) | |
| *A61K 9/00* | (2006.01) | |
| *A61K 9/48* | (2006.01) | |

(52) U.S. Cl.
CPC ............ *A61K 31/685* (2013.01); *A23L 33/10* (2016.08); *A23L 33/115* (2016.08); *A23L 33/12* (2016.08); *A61K 9/0053* (2013.01); *A61K 9/4858* (2013.01); *A61K 9/4866* (2013.01); *A61K 9/4875* (2013.01); *A61K 35/612* (2013.01); *A23V 2002/00* (2013.01)

(58) Field of Classification Search
CPC ..................... A61K 31/685; A61K 35/612
See application file for complete search history.

(56) References Cited

U.S. PATENT DOCUMENTS

| | | | |
|---|---|---|---|
| 2006/0128665 A1* | 6/2006 | Leigh ................ | A23D 9/013 514/78 |
| 2008/0058286 A1 | 3/2008 | Bruheim | |
| 2012/0149867 A1 | 6/2012 | Bruheim et al. | |
| 2013/0095142 A1 | 4/2013 | Shin | |

FOREIGN PATENT DOCUMENTS

| | | |
|---|---|---|
| CN | 102987382 A | 3/2013 |
| JP | 2909508 B2 * | 6/1999 |
| WO | 2008/017957 | 2/2008 |
| WO | 2008/117062 | 10/2008 |
| WO | 2009/027692 | 3/2009 |
| WO | 2010/035013 | 4/2010 |
| WO | 2010/097701 | 9/2010 |
| WO | 2011/050474 | 5/2011 |
| WO | 2011/051743 | 5/2011 |
| WO | 2012/172411 | 12/2012 |
| WO | 2013/093630 | 6/2013 |
| WO | 2013/102792 | 7/2013 |
| WO | 2013/127727 | 9/2013 |
| WO | 2014/014766 | 1/2014 |
| WO | 2014/057362 | 4/2014 |
| WO | 2014/207571 | 12/2014 |
| WO | 2015/104401 | 7/2015 |

OTHER PUBLICATIONS

Kidd, P. Alternative Medicine Review vol. 12, No. 3. p. 207-227. (Year: 2007).*
Batetta B et al. "Endocannabinoids may mediate the ability of (n-3) fatty acids to reduce ectopic fat and inflammatory mediators in obese Zucker rats." (2009) J Nutr 139(8):1495-1501.
Homan R et al. "Rapid separation and quantitation of combined neutral and polar lipid classes by high-performance liquid chromatography and evaporative light-scattering mass detection" (1998) J Chromatogr B Biomed Sci Appl 708:21-26.
Moreau et al. "The analysis of lipids via HPLC with a charged aerosol detector." (2006) Lipids 41:727-734.
Watanabe et al. "Effective Components in Cuttlefish Meal and Raw Krill for Improvement of Quality of Red Seabream Pagrus major Eggs" (1991) Nippon Suisan Gakkaishi 57:681-94.
Winther et al. "Elucidation of Phosphatidylcholine Composition in Krill Oil Extracted from Euphausia superba" (2011) Lipids 46:25-36.
International Search Report, International Patent Application No. PCT/EP2015/053024, dated Mar. 26, 2015.
Ali-Nehari et al. "Characterization of purified phospholipds from krill () residues deoiled by supercritical carbon dioxide" Korean Journal of Chemical Engineering, vol. 29, No. 7, 2012, pp. 918-924.

* cited by examiner

*Primary Examiner* — Amy L Clark
(74) *Attorney, Agent, or Firm* — Casimir Jones S.C.; J. Mitchell Jones

(57) ABSTRACT

Oral capsules have been dismissed as a dosage form for delivery high dosages of krill phospholipids, but by purifying these to high levels it is indeed possible to use this dosage form to deliver, for example, 700 mg or more phospholipids per capsule.

7 Claims, No Drawings

CAPSULES CONTAINING HIGH DOSES OF KRILL PHOSPHOLIPIDS

This application is a U.S. 371 national phase entry of International Patent Application No. PCT/EP2015/053024, international filing date Feb. 12, 2015, which claims the benefit of United Kingdom patent application 1402457.4 filed Feb. 12th 2014, the complete contents of which are incorporated herein by reference for all purposes.

TECHNICAL FIELD

The invention relates to pharmaceutically acceptable capsules for oral administration of high doses of krill phospholipids.

BACKGROUND OF THE INVENTION

There is accumulating evidence of the benefits of dietary intake of the long chain omega-3 fatty acids found in fish, docosahexaenoic acid (DHA) and eicosapentaenoic acid (EPA). These fatty acids have been shown to decrease the risk of coronary heart disease and ischemic heart disease, and the products Lovaza®, Omacor®, and Vascepa® are approved for human use.

The molecular form of omega-3 fatty acids (e.g. triglycerides or ethyl esters) may be important to their biological effect and their distribution in the body. Krill oil contains a high proportion of omega-3 fatty acids incorporated in phospholipids and it has been demonstrated that krill oil had stronger effects than fish oil on specific parameters related to metabolic syndromes [1]. Moreover, krill is abundant, can be harvested easily, and is very low in the food chain which results in a relative lack of pollution-derived contaminants.

The concentration of phospholipids in commercially available krill oils is relatively low (e.g. less than 500 mg/mL in Superba™ oil). Reference 2 considered the problem of delivering high doses of omega-3 phospholipids in the form of krill oil and, after reviewing the ways in which these oils have formulated, concluded that the most common prior art dosage form (the oral capsule) was disadvantageous for many reasons. Thus reference 2 instead proposed a powder or tablet formulation which can provide oral dosage forms "having a high concentration of the desired krill oil".

Powders were also proposed in reference 3, and further alternatives to capsules have also been suggested, including emulsions (e.g. see references 4 & 5).

It is an object of the invention to provide further and improved ways of delivering high doses of krill phospholipids.

DISCLOSURE OF THE INVENTION

The inventors' aim was to deliver high doses of krill phospholipids. Although reference 2 has dismissed the suitability of capsules for achieving this goal, the inventors have realised that by using krill phospholipids which are prepared at high purity it is indeed possible to use oral capsules for delivering high doses of krill phospholipids to humans e.g. 700 mg or more phospholipids per capsule (compared with a maximum of 267 mg krill oil per tablet in reference 2).

This high dosage in capsules has not previously been possible for at least two reasons. Firstly, the relatively low purity of phospholipids within krill oil products meant that a 700 mg dose would not fit inside a capsule which is suitable for human oral administration. Secondly, high-purity phospholipids have not been available in a form which is amenable to current encapsulation techniques e.g. they are waxy solids which either (i) could not be pumped within capsule-filling machines, or (ii) when converted to powder form, the necessary excipients reduce the krill oil content to less than 25% by weight of the powder [2], thus giving a lower dosage density than in existing krill oils (e.g. around 50% by weight phospholipids in Superba™ oil).

Thus the invention provides for the first time a pharmaceutically acceptable oral capsule for human use including between 700-1200 mg krill phospholipid.

These capsules can be prepared most easily by encapsulating a liquid composition containing a high concentration of highly-purified krill phospholipids, and also by avoiding unnecessary empty space within the capsule. Suitable liquid compositions can be prepared by combining highly-purified krill phospholipids with a viscosity-reducing agent which can give a mixture having flow properties which are compatible with the machinery used for preparing oral capsules. By following the guidance herein, viscosity can be maintained within a useful range while using a low amount of viscosity-reducing agents, thereby providing a high concentration of phospholipids within the liquid and thus permitting a high amount of phospholipids (i.e. 700 mg or more) to be encapsulated even within the limited volume which is available in capsules suitable for human oral administration.

Oral Capsules

The invention is concerned with preparing pharmaceutically acceptable oral capsules for human administration. These take the form of hollow shells, within which liquid contents (liquid at least at the time of filling into the shells) containing krill phospholipids are encapsulated. They are intended to be swallowed whole by a patient, after which the shell breaks down and releases the capsule's contents into the gastrointestinal tract.

The invention can be used with both hard capsules and soft capsules. Hard capsules are made of two shells: the capsule body and a cap. The cap fits snugly over the open end of the capsule body, thereby forming the enclosed shell. To ensure reliable closing of the filled capsules, shells with locking grooves or indentations are often used. The grooves or indentations fit into each other for tight closing and they prevent accidental separation of the assembled capsule. The joint between the two capsule parts can be sealed (e.g. with a gelatin or polymer band, or via thermal bonding). Hard capsules are typically made from gelatin, but gelatin-free hard capsules are also known e.g. made from hypromellose (hydroxypropyl methylcellulose; HPMC), pullalan, PVA copolymer, or starch. Mixtures of materials can also be used e.g. gelatin and polyethylene glycol, HPMC and carrageenan, HPMC and pectin, etc. In addition to these materials, hard capsules can include colourings, water, plasticizers, sugars, etc.

Where the invention uses a hard capsule, it should have a size and shape which are amenable to human swallowing. Hard capsule shells are manufactured in various standard sizes. For human use, capsules ranging in size from 000 (the largest) to 5 (the smallest) are commercially available. Details of standard capsule sizes are below [6], although details and tolerances may vary by manufacturer:

| Size | 000 | 00 | 0 | 1 | 2 | 3 | 4 | 5 |
|---|---|---|---|---|---|---|---|---|
| Volume (mL) | 1.37 | 0.95 | 0.68 | 0.50 | 0.37 | 0.30 | 0.21 | 0.13 |
| Length (mm) | 26.14 | 23.3 | 21.7 | 19.4 | 18.0 | 15.9 | 14.3 | 11.1 |
| Outer diameter (mm) | 9.91 | 8.53 | 7.65 | 6.94 | 6.35 | 5.82 | 5.31 | 4.91 |

Where the invention uses a hard capsule, it is typically of size 000 or 00, with size 00 being preferred. For any size of capsule the invention permits higher doses to be delivered than has previously been possible because it uses krill phospholipids of higher purity.

The invention can also use soft capsules. These are one-piece hermetically-sealed soft shells, typically prepared by a rotary-die process in which two continuous gelatin ribbons are brought together between twin rotating dies, where material is injected between the ribbons as they form the shell within the dies. The two sheets are sealed by pressure and heat and then separated from the ribbons. Drop formation processes are also used, which can provide seamless capsules. Soft capsules generally have thicker shells than hard capsules. They are typically made from gelatin, but gelatin-free hard capsules are also known e.g. made from starches, carrageenans, or combinations thereof. In addition to these materials, soft capsules usually include a plasticizer (e.g. sorbitol, xylose, maltitol, glycerin), and they can also include colourings, water, and sugars. Soft capsules can be preferred for volatile liquid contents or for materials which are susceptible to deterioration in the presence of air. Thus soft capsules are preferred for the present invention. Soft gelatin capsules which include glycerol as a plasticiser can be used, and in this situation it is advantageous that the liquid contents should also include glycerol.

Where the invention uses a soft capsule, it should have a size and shape which are amenable to human swallowing. Soft capsules come in various shapes (including spherical/round, oval/elliptical, and oblong) and sizes, including various standard sizes including 4 round, 5 round, 6 round, 7 round, 6 oval, 7 oval, 10 oval, 20 oval, 6 oblong, 8 oblong, 9.5 oblong, 5 tube, 6 tube, and 8 tube etc. (e.g. see chapter 13 of ref. 7). The number in these size designations represents the maximum internal volume of the capsule in minims (where 16.23 minims=1 mL) e.g. a 12 oval capsule can encapsulate up to 0.74 mL material. Soft capsules used with the invention should ideally have a size designation within the range 14-30 or 15-25 (14 minims=0.863 mL; 15 minims=0.924 mL; 25 minims=1.540 mL; 30 minims=1.848 mL) e.g. 15, 16, 17.5, 20, 28, or 30.

The amount of krill phospholipids per capsule is within the range 700-1200 mg e.g. within the range 750-1000 mg, or 800-900 mg. For example, a capsule can contain 700, 750, 800, 850, 900, 950, 1000, 1050, 1100, 1150, or 1200 mg.

The materials used to make the capsules should be pharmacopoeial-grade e.g. USP or PhEur. Pharmacopoeial-grade gelatins and starches are routinely available.

Capsule Filling Process

The normal process for preparing a hard oral capsule involves inserting the desired contents into the body, and then fitting the cap. To prevent leakage of liquid contents the joint between body and cap can then be sealed. The normal process for preparing a soft capsule is discussed above. For both operations the reduction in viscosity provided by the invention gives material which can be handled easily by existing machinery for filling capsules. Unfortunately, the addition of a viscosity-reducing agent tends to increase hygroscopicity, thereby leading to higher levels of lysophospholipids which emerge during storage (although still at very low levels overall, e.g. ≤1%).

One way to address this issue is to use a volatile solvent as part of the viscosity-reducing agent. This permits viscosity to be reduced (as discussed above) while the capsules are being filled, as desired. Once the capsule has been sealed, however, the inventors have observed that volatile solvents can escape from the capsules during storage (particularly under drying conditions), which means that viscosity of the contents increases again, which leads to less water entry and thus a longer shelf-life.

The invention therefore provides a process comprising steps of: (a) mixing (i) a phospholipid-containing krill extract which has a viscosity of at least 3000 mPa·s at 25° C. with (ii) a volatile solvent, to give a liquid composition having a viscosity of less than 3000 mPa·s at 25° C.; (b) inserting this liquid composition into a capsule; and (c) storing the capsule under conditions such that at least a portion of the volatile solvent escapes from the capsule such that viscosity of the capsule's contents increases to at least 3000 mPa·s at 25° C.

This process can be used to provide an advantageous oral capsule whose contents include purified krill phospholipids, wherein the contents have a viscosity of at least 3000 mPa·s at 25° C.

Step (a) of the process is the same as discussed above, except that the viscosity-reducing agent must comprise a volatile solvent. Suitable solvents include lower alcohols as discussed above, such as ethanol. The volatile solvent will typically not be used on its own e.g. a mixture of ethanol with PEG, MCTs, or glycerol can be used. The viscosity-reducing agent containing the volatile solvent reduces the viscosity of the phospholipid material.

This material is then inserted into a capsule, such as a soft capsule, as discussed above. Soft gelatin capsules are typical, as these can readily permit escape of volatile solvents.

Sealed capsules are then stored to permit the volatile solvent to escape from the capsule's contents. This can occur during the formal process of drying which follows capsule filling prior to packaging e.g. in a drying room. Drying for about 3 days is generally enough to permit solvent to escape, and thus for viscosity to increase. Typically, at least 20% (by weight) of the volatile solvent escapes from the capsules, and often even more e.g. ≥25%, ≥30%, ≥33%, or more.

Liquid Contents

Capsules of the invention encapsulate a liquid composition which comprises krill phospholipids. Typically, it will also include a viscosity-reducing agent (and, optionally, one or more further components).

The viscosity-reducing agent reduces the intrinsic viscosity of the purified phospholipids so that the mixture can be handled easily for preparing oral capsules. Ideally, the mixture has a viscosity (dynamic viscosity) within the range 10-3000 mPa·s at a temperature within the range 25-70° C. Thus, within at least a portion of this temperature range, the mixture will exhibit a viscosity within this range, but it is not necessary that the mixture has this viscosity across the complete temperature range. For instance, it might have a viscosity of >3000 mPa·s at 25° C. but a viscosity within the range of 10-3000 mPa·s at a higher temperature e.g. at 40° C. or above. Thus the composition can retain the useful liquid characteristics of known krill extracts while providing much higher concentrations of phospholipids.

Within the range of 10-3000 mPa·s, it is preferred that viscosity should not exceed 1000 mPa·s, so a viscosity within the range 50-1000 or 100-1000 mPa·s is a preferred option. Viscosity can be measured using a shear rate of 100 $s^{-1}$ over a period of 20 minutes.

In addition to this viscosity property, the mixture should remain homogeneous when subjected to shear stress at shear rates up to 100 $s^{-1}$. Thus the mixture remains liquid under these conditions, and does not undergo precipitation, crystallisation, or phase separation. The mixture therefore retains useful handling properties under shear conditions which could be experienced during the preparation of oral capsules.

To achieve these viscosity reductions, various viscosity-reducing agents can be mixed with the purified phospholipids, including hydrophilic additives, lipophilic additives, amphiphilic additives, and mixtures thereof. Suitable hydrophilic additives include, but are not limited to, lower alcohols (C1-C6 alcohols e.g. ethanol, 2-propanol, 1-propanol), benzyl alcohol, glycerol, and glycols (e.g. propylene glycol, or a polyethylene glycol such as PEG-300, PEG-400, or PEG-600). Suitable lipophilic additives include, but are not limited to, vegetable oils (e.g. castor oil, sesame oil), triglycerides (e.g. medium-chain triglycerides or MCTs, glyceryl trioctanoate, glyceryl trioleate, etc.). Suitable amphiphilic additives include, but are not limited to, surfactants such as polysorbates (e.g. polysorbate 80 or 20). Generally a viscosity-reducing agent will include two or three different components (see below).

In all cases the components of the viscosity-reducing agent should be pharmaceutically acceptable. Where an organic solvent is included, such as a lower alcohol, it is preferred to use only those solvents which are regarded as safe in humans. Pharmaceutically acceptable organic solvents are classified in Q3C 'class 3' (i.e. acetic acid, heptane, acetone, isobutyl acetate, anisole, isopropyl acetate, 1-butanol, methyl acetate, 2-butanol, 3-methyl-1-butanol, butyl acetate, methylethyl ketone, tert-butylmethyl ether, methyl-isobutyl ketone, cumene, 2-methyl-1-propanol, dimethyl sulfoxide, pentane, ethanol, 1-pentanol, ethyl acetate, 1-propanol, ethyl ether, 2-propanol, ethyl formate, propyl acetate, and formic acid). Thus compositions of the invention are preferably free from organic solvent components which are not in this list e.g. they should be free from chloroform and hexane (and optionally also free from dichloromethane). Thus, where a composition of the invention includes an organic solvent (whether as a residual component in the phospholipids or as a component of the viscosity-reducing agent), this is preferably a 'class 3' solvent, and it is even more preferred that a composition should include only 1 or 2 organic solvents in total e.g. only ethanol.

The amounts of viscosity-reducing agent which is used to achieve the desired reduction in viscosity can readily be determined by following the guidance given herein. To maximise the phospholipid concentration within the liquid, however, the amount of viscosity-reducing agent should be kept to a low level. Ideally, the proportion of viscosity-reducing agent should be no more than 20% by weight of the liquid composition e.g. within the range of 5-15%. Thus, for instance, the liquid material can include from 5-20% by weight viscosity-reducing agent and from 80-95% by weight krill oil extract, wherein the krill oil extract includes 85% by weight or more of krill phospholipids.

To achieve the desired viscosity with such low levels of viscosity-reducing agent, it is preferred to use a mixture of two components as the viscosity-reducing agent. Typically, a lower alcohol will be included within the range of about 2-10% by weight of the liquid composition (e.g. 5-10%) as part of the viscosity-reducing agent, and also a second additive (e.g. MCTs or a PEG) within the range of 5-10% by weight of the liquid composition. The remainder of the liquid composition can be krill oil with a high content of purified phospholipids. As mentioned below, where the second additive is a PEG, the alcohol can be used at lower concentrations, thereby permitting higher phospholipid concentrations to be achieved.

Some embodiments of the invention use a viscosity-reducing agent which comprises a hydrophilic additive (such as a lower alcohol) and a lipophilic additive. For example, the viscosity-reducing agent can be a mixture of ethanol and MCTs. MCTs are a mixture of triglycerides of saturated fatty acids, mainly of caprylic acid and capric acid, and can include a minimum of 95% by weight of $C_8$ and $C_{10}$ saturated fatty acids. They are usually obtained from coconut oil or palm kernel oil.

Such mixtures give useful viscosity, but they tend to require quite high levels of alcohols (e.g. above 5%) and of triglycerides, and thus lower concentrations of phospholipids. Thus it may be preferred to use a viscosity-reducing agent which comprises a lower alcohol and a further hydrophilic additive (e.g. a glycol) as lower amounts of these agents can achieve the same viscosity reduction. For instance, a lower alcohol such as ethanol can usefully be combined with a polyethylene glycol (PEG) or propylene glycol. PEGs having a molecular weight of less than 1000 can be used, and both PEG400 and PEG300 (i.e. PEGs with an average molecular weight of 400 and 300, respectively) have provided useful viscosity reductions even with only 2.5% or 5% by weight ethanol and 12.5% by weight PEG400.

One useful viscosity-reducing agent is based on a mixture of PEG, MCTs, and glycerol. Mixtures of PEG and glycerol, and of MCTs and glycerol, are also useful. A mixture of ethanol with one or more of PEG, MCTs, and glycerol can also be used. PEG600 is preferred in these mixtures.

By keeping the amount of viscosity-reducing agent low (e.g. less than 20% or 15% by weight, or even 10% or less), the amount of phospholipids can be correspondingly high. With ≥80% by weight of a krill oil which includes ≥85% by weight krill phospholipid, the liquid can include ≥680 mg/mL of krill phospholipids. With lower amounts of viscosity-reducing agent and higher purity of phospholipids within a krill extract, the concentration of krill phospholipids can reach 900 mg/mL or more. Thus a liquid composition of the invention can include krill phospholipids at a concentration within the range 680-900 mg/mL e.g. ≥700 mg/mL, ≥750 mg/mL, ≥800 mg/mL, or ≥850 mg/mL, or higher. For instance, the concentration can be between 720-850 mg/mL. In contrast, the concentration of krill phospholipids in Superba™ capsules is less than 500 mg/mL. At a concentration of 680 mg/mL a dose of 700 mg krill phospholipids can be achieved in a volume of 1.03 mL, which will fit easily in a soft gel capsule of a size of 17-20 minims (i.e. 1.047-1.232 mL) or inside a size 00 capsule with a small amount of overfill. At a slightly higher concentration of 765 mg/mL (85% by weight of a krill oil having 90% phospholipids) a 700 mg dose has a volume of 0.915 mL (14.85 minims), and at 855 mg/mL (90% by weight of a krill oil having 95% phospholipids) a 700 mg dose has a volume of only 0.82 mL (13.29 minims).

Phospholipids of high purity (i.e. where the phospholipids make up a high proportion of the krill material) can be prepared in various ways from krill oil e.g. see references 8-11. Purities of 85% by weight or more (weight of krill phospholipids out of total weight of lipids) can be achieved using these methods (e.g. 85%, 90%, 91%, 92%, 93%, 94%, 95%, 96%, 97%, 98%, 99% or more) and the invention uses krill phospholipids having such purity.

Ideally, the viscosity-reducing agent is not naturally present within krill oil, such that its presence immediately signifies that the composition goes beyond mere purification of phospholipids from krill. Even if the viscosity-reducing agent is similar to components present within krill oil, simple analysis can confirm that the composition is not merely a purified krill material e.g. by detecting the relative proportions of components. A mixture of purified krill phospholipids and a lipophilic viscosity-reducing agent (e.g.

MCTs) can easily be distinguished from less pure krill oil extracts (e.g. Superba™ or Onemia™) by analysis of its lipid composition. For instance, the fatty acid profile of MCTs differs from the fatty acid profile of the non-phospholipid fraction of krill oils.

The liquid compositions can be prepared by simple mixing of the purified krill phospholipids with and the viscosity-reducing agent. In some embodiments this mixing process can form a homogeneous suspension, but the invention ideally uses a clear solution i.e. the phospholipids are dissolved in the viscosity-reducing agent to give a clear solution having the desired properties. Where the viscosity-reducing agent includes more than one component, the mixing may take place in various stages e.g. mixing the phospholipids with a first component of the viscosity-reducing agent, and then mixing this intermediate mixture with a second component of the viscosity-reducing agent (for example, mix the phospholipids with MCTs, and then combine this mixture with ethanol) to give the final desired liquid composition.

Krill Phospholipids

Capsules of the invention include krill phospholipids. As noted above, krill phospholipids with purities of 85% by weight or more can be prepared. Preferred purification methods can reduce levels of impurities such as trimethylamine N-oxide (TMAO), astaxanthins, lysophospholipids, and free fatty acids, to give highly pure krill phospholipid compositions and increase the efficiency of their delivery by oral capsules.

The krill phospholipids can be from any species of krill, including Antarctic krill (*Euphausia superba*), Pacific krill (*Euphausia pacifica*) and Northern krill (*Meganyctiphanes norvegica*). In addition to *E. superba*, other species are known to live in the Antarctic, one in genus *Thysanoessa* (*T. macrura*) and six in genus *Euphausia*. These include ice krill (*Euphausia crystallorophias*), *E. frigida*, *E. longirostris*, *E. triacantha* and *E. vallentini*. The preferred krill species is *E. superba*.

The krill phospholipids used with the invention preferably comprise a mixture of phospholipid compounds of formula (I) as described in detail below:

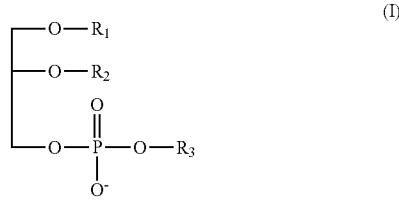

wherein:

$R_1$ and $R_2$ are each independently selected from a fatty acid moiety of formula $-COC_nH_m$, a fatty acid moiety of formula $-CH_2C_nH_m$, and $-H$;

$R_1$ and $R_2$ include omega-3 fatty acid moieties, such that at least 30% by weight of the phospholipid compounds is composed of omega-3 fatty acid moieties;

at least 90% by weight of total omega-3 fatty acid moieties are at position $R_2$;

$R_1$ and $R_2$ are not both $-H$ in a phospholipid compound, and $R_1$ or $R_2$ is $-H$ in less than 15% by weight of the compounds of formula (I), and ideally in less than 3% by weight of the compounds of formula (I);

$R_3$ is selected from $-H$, a choline moiety, an ethanolamine moiety, a N-acetylethanolamine moiety, an inositol moiety, and a serine moiety; and $R_3$ is a choline moiety in at least 85% by number of the compounds of formula (I).

Typically, and as explained in more detail below, the krill phospholipids compositions used with the invention also have one or more of the following properties:

(a) at least 85% by weight of the composition consists of phospholipid compounds of formula (I);
(b) the weight ratio of C16:0/C14:0 fatty acid moieties in the mixture is between 10:1 and 18:1 and/or the weight ratio of C18:4 n−3/C18:3 n−3 fatty acid moieties is between 1:1 and 3:2;
(c) the composition includes less than 300 μg astaxanthins per gram of phospholipid;
(d) the composition comprises less than 0.01% by weight trimethylamine N-oxide
(e) the composition comprises less than 0.01% by weight homarine;
(f) the composition includes less than 5% by weight water;
(g) the composition has less than about 0.03% by weight PUFA polymers
(h) the phospholipid mixture includes both phospholipids where $R_1$ is a fatty acid moiety of formula $-COC_nH_m$ and phospholipids where $R_1$ is a fatty acid moiety of formula $-CH_2C_nH_m$;
(i) the phospholipid mixture includes both phospholipids where $R_1$ is an omega-3 fatty acid moiety and phospholipids where $R_2$ is an omega-3 fatty acid moiety;
(j) the composition includes less than 5% by weight sphingomyelin; and/or
(k) the composition is free from chloroform and hexane.

$R_1$ and $R_2$ $R_1$ and $R_2$ are each independently selected from the group consisting of a fatty acid moiety of formula $-COC_nH_m$, a fatty acid moiety of formula $-CH_2C_nH_m$, and $-H$. $R_1$ or $R_2$ is $-H$ in only a small fraction of the compounds of formula (I) i.e. less than 3% by weight of the phospholipid compounds are lysophospholipids (see below). Thus most $R_1$ and $R_2$ are $-COC_nH_m$ or $-CH_2C_nH_m$. Where $R_1$ or $R_2$ has formula $-COC_nH_m$ the fatty acid moiety has an ester linkage, but where $R_1$ or $R_2$ has formula $-CH_2C_nH_m$ the fatty acid moiety has an ether linkage. In these formulae $C_nH_m$ refers to the aliphatic chain which is seen in a naturally-occurring fatty acid (e.g. as seen in krill). For any value of n, m=2n+1 when the fatty acid moiety's aliphatic chain is saturated, but m is reduced by 2 for each unsaturated bond (double bond) in the aliphatic chain i.e. m=2n−1 if one unsaturated bond is present, m=2n−3 if two double bonds are present, m=2n−5 if three double bonds are present, etc. Thus, in general, n is an integer in the range of 4-24 and m=2(n−p)+1, where p is the number of double bonds in the fatty acid moiety. As disclosed in reference 12, the value of n for krill is generally within the range of 11 to 21, and krill phospholipids can include fatty acid moieties with up to six double bonds.

Typically, where a fatty acid moiety at position $R_1$ or $R_2$ is of formula $-CH_2C_nH_m$, the fatty acid moiety is either saturated or monounsaturated. Thus, where $R_1$ or $R_2$ is of formula $-CH_2C_nH_m$, the relationship between n and m is m=2n±1 at that position. In a single molecule, however, it is possible to have a fatty acid moiety of formula $-COC_nH_m$ at one of $R_1$ and $R_2$ (i.e. ester-linked) and a fatty acid moiety of formula $-CH_2C_nH_m$ at the other of $R_1$ and $R_2$ (i.e. ether-linked). Furthermore, usually 90% (molar) or more of the ether-linked fatty acid moieties will generally be C16 and/or C18 (i.e. where n=15 or 17), unsaturated (e.g. C16:0) or monounsaturated (e.g. C18:1), and ether-linked omega-3 fatty acid moieties are generally not present. Overall, within the mixture, it is preferred that no more than 10% by number of the fatty acid moieties are of formula —$CH_2C_nH_m$ (i.e. 10% or fewer of fatty acid moieties are ether-linked, and more than 90% are ester-linked). It is preferred, though, that the phospholipid mixture should include ether-linked fatty acid moieties i.e. they should not be undetectable. Ether-linked fatty acid moieties are readily detected and quantified by NMR (e.g. see reference 12).

In general, $R_1$ and $R_2$ are not both of formula —$CH_2C_nH_m$ in any single phospholipid molecule. Furthermore, fewer than 5% by number (e.g. fewer than 1% by number, or even zero) of the phospholipid molecules in the mixture have $R_2$ of formula —$CH_2C_nH_m$. In other words, ether-linked fatty acid moieties within the mixture may be seen at $R_1$, but not at $R_2$. Thus, in some embodiments: $R_1$ is selected from a fatty acid moiety of formula —$COC_nH_m$, a fatty acid moiety of formula —$CH_2C_nH_m$, and —H; and $R_2$ is selected from a fatty acid moiety of formula —$COC_nH_m$, and —H.

In some embodiments: $R_1$ is selected from a fatty acid moiety of formula —$COC_nH_m$, a fatty acid moiety of formula —$CH_2C_nH_m$ where m=2n+1, and —H; and $R_2$ is selected from a fatty acid moiety of formula —$COC_nH_m$, and —H. Thus, within the mixture: $R_1$ is an ester-linked fatty acid, an ether-linked saturated or monounsaturated fatty acid, or hydrogen; and $R_2$ is either an ester-linked fatty acid moiety or hydrogen; provided that $R_1$ and $R_2$ are not both hydrogen in a single molecule.

The term "fatty acid" as used herein refers to a carboxylic acid with an unbranched aliphatic chain, which may be saturated or unsaturated. These have the general formula $C_nH_m$—COOH. Long chain polyunsaturated fatty acids (LC-PUFAs) are in general fatty acids that have a n value of 19 or more. Polyunsaturated refers to unsaturation at two or more bonds. The term "fatty alcohol" refers to an alcohol with an unbranched aliphatic chain, which may be saturated or unsaturated, and they have the general formula $C_nH_m$—$CH_2OH$. The term "fatty acid moiety" as used herein refers to the aliphatic chain $C_nH_m$ from such fatty acids and fatty alcohols, and the nature of the moiety can be defined by referring to the corresponding fatty acid and/or fatty alcohol. Thus, for a fatty acid moiety of formula —$COC_nH_m$ or —$CH_2C_nH_m$ the corresponding fatty acid is $C_nH_m$—COOH and the corresponding fatty alcohol has formula $C_nH_m$—$CH_2OH$. By way of example the fatty acid DHA ($C_{21}H_{31}$COOH) corresponds to a fatty acid moiety of formula —$COC_{21}H_{31}$ or —$CH_2C_{21}H_{31}$, and EPA ($C_{19}H_{29}$COOH) corresponds to a fatty acid moiety of formula —$COC_{19}H_{29}$ or —$CH_2C_{19}H_{29}$.

$R_1$ and $R_2$ can thus be fatty acid moieties that contain saturated or unsaturated aliphatic chains, but at least 30% by weight of the phospholipid mixture is composed of omega-3 fatty acid moieties at the $R_1$ and $R_2$ positions (i.e. omega-3 fatty acid moieties provide at least 30 g for every 100 g of phospholipid compounds in the mixture). Omega-3 fatty acids are polyunsaturated fatty acids whose final double bond is positioned between the third and fourth carbon atoms from the methyl end of the hydrocarbon chain. Non-limiting examples of omega-3 fatty acids include 5,8,11,14,17-eicosapentaenoic acid (EPA), 4,7,10,13,16,19-docosahexanoic acid (DHA) and 7,10,13,16,19-docosapentaenoic acid (DPA). At least 90% by weight of total omega-3 fatty acid moieties in a phospholipid mixture are at position $R_2$ within formula (I). At least 50% by weight of total omega-3 fatty acid moieties in a phospholipid mixture are EPA and/or DHA (i.e. weight of DHA and EPA/total weight of omega-3 fatty acid moieties in the phospholipids of formula I).

The weight contribution of total omega-3 fatty acid moieties at the $R_1$ and $R_2$ positions can be determined by extracting total phospholipids from the mixture e.g. using the method of reference 13. This is followed by hydrolysis of the lipids to release fatty acids. The released fatty acids are converted to fatty acid esters e.g. fatty acid methyl esters and these esters are analysed e.g. by gas chromatography, HPLC, etc. For instance, the American Oil Chemists' Society has published AOCS Official Method Ce 1b-89 for determining the fatty acid composition of marine oils and marine oil esters by capillary column gas-liquid chromatography. Similarly, reference 12 discloses quantitative analysis of krill oil using HPLC methods based on references 14 and 15 (using evaporative light scattering detection or charged aerosol detection). These established methods provide the amount of specific fatty acids present in a sample, from which the amount of omega-3 fatty acids present in the sample (i.e. in positions $R_1$ and $R_2$ of the phospholipid mixture) can be calculated. In general, references to the content of lipid or phospholipid compositions on a weight/weight basis as referred to herein should be taken as having been determined on the basis of these methods (extraction as in reference 13, followed by processing and analysis by chromatography).

Preferably the phospholipid mixture comprises between 30-40% w/w omega-3 fatty acid moieties.

In some embodiments, the phospholipid mixture comprises both EPA and DHA fatty acid moieties, in which case the EPA and DHA moieties are preferably present in a molar ratio of EPA:DHA of from about 1:1 to about 3:1 (e.g. about 1.5:1 to 2:1 or about 1.8:1 to 2.2:1).

Phospholipid mixtures used with the invention differ from reference 16, where $R_1$ and/or $R_2$ is/are —OH 20-50% of the phospholipids, rather than being a fatty acid moiety, and where transesterification is used to provide a mixture having as much as 35% lysophospholipids.

Lysophospholipids are formed by hydrolysis of fatty acids from phospholipids, resulting in phospholipids with a single fatty acid moiety. Thus one of $R_1$ or $R_2$ is —H in these lysophospholipid compounds. The invention seeks to avoid high levels of lysophospholipids, and the processes of the invention result in low concentrations of lysophospholipids, namely ≤3% w/w and preferably less than 2%, less than 1%, or even less than 0.5% (weight of lysophospholipid/weight of total phospholipids of formula I). The amount of lysophospholipid may be determined by the HPLC-based analytical methods referred to above, and also by NMR or HP-TLC.

In one embodiment the mixture has a lysophospholipid content of between 1.1-3% w/w, but in other embodiments the mixture has a lysophospholipid content of less than 0.9% w/w. In some embodiments, however, the mixture can have a lysophospholipid content much higher than this, but less than 15% w/w e.g. <10%, or <5%. In general, however, a lysophospholipid content of less than 3% w/w, and typically <2% or <1%. Lysophospholipids are surfactants and they cause the formation of micelles and tubular systems in the presence of water, which leads to a change in rheological properties and, in particular, an increase in viscosity, so their presence is not desirable.

$R_1$ and $R_2$ are not both —H in a phospholipid compound. Furthermore, within the composition, it is preferred that molecules of formula (I) where $R_1$ and $R_2$ are both hydrogen are undetectable.

$R_3$ $R_3$ is H or is selected from a choline, ethanolamine, N-acetylethanolamine, inositol and serine. Choline moieties predominate at $R_3$, and the mixture of phospholipid compounds comprises more than 80% choline moieties at position $R_3$ on a molar % basis (mol of choline moieties/total mol phospholipid compounds of formula I), and preferably more than 85% e.g. at least 86, 87, 88, 89, or 90% choline moieties at position $R_3$ on a molar % basis. The mixture of phospholipid compounds can comprise at least 1% (e.g. about 3-15%, 5-12%, 7-10% or 8-9%) ethanolamine and/or N-acetylethanolamine moieties at position $R_3$ on a molar % basis, and preferably a mixture includes at $R_3$ choline and either or both of ethanolamine and/or N-acetylethanolamine. The mixture of phospholipid compounds can comprise <1% of inositol moieties at position $R_3$ on a molar % basis. These amounts can be determined for example by using NMR. The methods referred to above can also be used to determine the amounts of these components on a w/w basis (in which the amount of each may be expressed in g/100 g oil).

Within the mixture, for molecules where $R_3$ is a choline moiety, it is preferred that around 5-15% by number of these molecules have an ether-linkage at position $R_1$. Thus, where $R_3$ is choline, 5-15% of these molecules have $R_1$ of formula —$CH_2C_nH_m$, where m=2n±1.

Within the mixture, for molecules where $R_3$ is an ethanolamine or N-acetylethanolamine moiety, it is preferred that around 35-45% by number of these molecules have an ether-linkage at position $R_1$. Thus, where $R_3$ is ethanolamine or N-acetylethanolamine, 35-45% of these molecules have $R_1$ of formula —$CH_2C_nH_m$, where m=2n+1.

Phosphorous-containing groups in phospholipids used with the invention may exist in a number of protonated and deprotonated forms depending on the pH of the surrounding environment, for example the pH of the solvent system in which they are dissolved. Therefore, although a particular form may be illustrated in the formula shown above with a negatively-charged $O^-$ group, this is intended to be merely representative and does not limit the invention to a specific protonated or deprotonated form.

Phospholipid Concentration

In some embodiments at least 85% by weight of a krill-derived composition consists of phospholipid compounds of formula (I) e.g. >90%, >95%, >96%, >97%, >98%, or even >99%. The low level of impurities means that such compositions are particularly suitable for pharmaceutical use.

These highly pure compositions can be obtained via the use of acetone precipitation, but it is preferred that the compositions are substantially free from residual acetone. Acetone is classified by ICH guideline Q3C as a class 3 solvent i.e. as having low toxic potential. Recommended intake of such solvents is 50 mg per day or less, and so a composition of the invention ideally has an acetone content of less than about 0.5% by weight e.g. less than 0.1%, or less than 0.01%. Acetone removal is very efficient and can achieve levels as low as 20 mg per kg of purified krill phospholipid (i.e. 0.002% by weight or 20 ppm). Alternatively defined, the phospholipids used with the invention can be essentially free from acetone.

Although preferred compositions are those in which, as discussed above, at least 85% by weight of the composition consists of phospholipid compounds of formula (I), in some embodiments this figure may be reduced, and the invention also contemplates compositions in which at least 75% or 80% by weight of the composition consists of phospholipid compounds of formula (I).

Fatty Acid Signature

A phospholipid mixture used with the invention can have: (i) a weight ratio of C16:0/C14:0 fatty acid moieties of between 10:1 and 18:1 e.g. between 12:1 and 16:1; and/or (ii) a weight ratio of C18:4 n–3/C18:3 n–3 fatty acid moieties of between 1:1 and 3:2. In these embodiments the phospholipid mixture does include (i) both C16:0 and C14:0 fatty acid moieties and/or (ii) both C18:4 n–3 and C18:3 n–3 fatty acid moieties.

Astaxanthins

Contrary to the preference in reference 8, where krill phospholipids include 3 g/kg astaxanthins, phospholipids used with the invention ideally include very low levels of astaxanthins (i.e. free astaxanthin and esters thereof) because, despite their advantageous antioxidant properties, the inventors see these compounds as pharmacological impurities which have a biological effect. The phospholipids used with the invention can have a concentration of astaxanthins which is less than 300 μg per gram of phospholipid (i.e. less than 0.03% by weight), and preferably less than 0.01% by weight. Phospholipids used with can even have less than 0.002% by weight astaxanthins (i.e. <20 mg astaxanthins per kg phospholipids) or less than 0.001%. Astaxanthin content can be measured by HPLC e.g. using UV detection.

Levels of astaxanthins are expressed herein as diol equivalents i.e. as free astaxanthin, without including the weight of any esterification (e.g. to fatty acids).

TMAO

In some embodiments phospholipids used with the invention comprise less than 0.01% by weight TMAO e.g. 0.005%. Ideally, TMAO is undetectable. TMAO is removed primarily by washing step (b). TMAO levels can also be expressed relative to the phospholipid compounds. As such the TMAO content can be expressed as a molar ratio such that compositions of the invention have a molar excess of phospholipids to TMAO of at least 1,000.

In addition to having low or no TMAO, compositions of the invention can also have less than 0.005% by weight trimethylamine (TMA) e.g. undetectable TMA.

TMA and TMAO can contribute to an unpleasant smell in a composition, and they can also lead to undesirably high viscosity.

Homarine

Homarine (N-methylpicolinic acid) is a morphogenetically active quaternary ammonium base which occurs in tissues of various marine animals, including krill. In some embodiments phospholipids used with the invention comprise less than 0.01% by weight homarine e.g. 0.005%. Ideally, homarine is undetectable.

Water Content

Phospholipids used with the invention can have a water content of less than about 5% w/w, and preferably less than about 4, 3, 2, or 1% w/w. Ideally, a composition of the invention is as dry as possible, so a water content of <2% w/w, such as <1% or even <0.5% is desirable. The phospholipids are quite hygroscopic in pure form, though, so they should be stored appropriately and can be re-dried after storage prior to being used for preparing compositions as disclosed herein.

PUFA Polymers

In some embodiments phospholipids used with the invention have a low concentration of polymers of polyunsaturated fatty acids. Preferably they have less than about 0.03, 0.02, or 0.01% w/w PUFA polymers. Polymer content is measured e.g. by NMR or gel permeation chromatography.

Sphingomyelins

Sphingomyelins are sphingophospholipids found in animal cell membranes. They are based on sphingosine, which is an 18-carbon amino alcohol with an unsaturated hydrocarbon chain, and they usually consist of phosphocholine and ceramide, or a phosphoethanolamine head group. Reference 9 discloses a krill polar lipid extract obtained using hexane and acetone, including 8% sphingomyelins. Phospholipids used with the invention can include less than 5% by weight sphingomyelin, or less than 4%, and generally include much less than this (or even zero). Thus phospholipids used with the invention may include less than 1% by wt sphingomyelin e.g. <0.1%, <0.01%, or <0.001%.

Residual Organic Solvents

As mentioned above, it is preferred in compositions of the invention to use only pharmaceutically acceptable solvent components which are regarded as safe in humans. Thus phospholipid compositions used with the invention are preferably free from organic solvent components which are not in this list e.g. they should be free from chloroform and hexane. If a phospholipid composition includes a residual organic solvent, this is preferably a 'class 3' solvent, and it is even more preferred that a composition with residual organic solvent should include residues of only 2 or 3 organic solvents in total e.g. residue only of ethanol and acetone.

Omega-6 Fatty Acid Moieties

Omega-6 fatty acids can be inflammatory, so they are ideally kept at low levels in compositions of the invention. Thus in some embodiments of the invention the total amount of omega-6 fatty acids (in particular those contributed by the phospholipid mixture) is less than 2% by weight, and ideally less than 1.5% or even less than 1%.

Starting Krill Materials for Preparing Phospholipids

For purifying phospholipids for use with the invention, rather than starting directly with krill organisms it is preferred to start with krill which have been processed e.g. as disclosed in any of references 17, 18, or 19. Dry or wet krill pastes can be made, but the preferred starting material is wet krill paste. As already known in the art (e.g. see example 4 of reference 17), such a paste can be obtained e.g. by heat treatment of krill organisms in water, separation of solid and aqueous materials by filtration to provide a krill milk, coagulation by heating, separation by filtration, and then pressing to remove water. A process of the invention can thus include an initial step of obtaining wet krill paste from live krill. Heating krill organisms soon after capture can inactivate their endogenous lipases, which can help to ensure that starting material used with the invention has a low intrinsic level of lysophospholipids, thereby reducing the need to remove these impurities during the process of the invention.

Preferred Phospholipid Mixtures

With reference to the features mentioned above, a preferred mixture of phospholipid compounds of formula (I) has properties (a), (c), (d), (h), and (k) as noted above. This composition preferably also has property (f) and/or properties (e) and (j). Thus a composition with all of properties (a), (c), (d), (e), (f), (h), (j), and (k) is particularly preferred.

With reference to property (h), fatty acid moieties of formula $-CH_2C_nC_m$ are either saturated or mono-unsaturated, and not polyunsaturated, such that m=2n+1. The value of n is from 11-21.

Usually, the compounds of formula (I) in such compositions will include (1) both C16:0 and C14:0 fatty acid moieties and/or (2) both C18:4 n−3 and C18:3 n−3 fatty acid moieties. Such compositions should also have characteristic (b) as noted above. Preferably the phospholipids include C16:0, C14:0, C18:4 n−3 and C18:3 n−3 fatty acid moieties.

When the mixture has property (f), the amount of water is ideally less than 2% by weight.

Further useful properties of these preferred mixtures are:
(l) the composition has less than 1% by weight free fatty acids;
(m) the composition has less than 0.005% by weight trimethylamine; and/or
(n) the composition is free from canthaxanthin and flavonoid.

Thus one preferred composition has properties (a), (b) (c), (d), (e), (f), (h), (j), (k), (l), (m), and (n), wherein: with reference to property (h) fatty acid moieties of formula $-CH_2C_nC_m$ are either saturated or mono-unsaturated, and not polyunsaturated; the compounds of formula (I) include C16:0, C14:0, C18:4 n−3 and C18:3 n−3 fatty acid moieties; and wherein the amount of water is optionally less than 2% by weight.

In these compositions the phospholipids of formula (I) can include EPA and DHA moieties in a molar ratio (EPA: DHA) of from 1.8:1 to 2.2:1.

Medical Uses of Capsules of the Invention

Capsules of the invention are pharmaceutically acceptable for human beings, and the invention provides a capsule of the invention for use in medicine.

The invention also provides the use of purified krill phospholipids in the manufacture of an oral capsule for human use including between 700-1200 mg krill phospholipid The invention also provides a method for treating a human subject, comprising a step of administering to the subject a capsule of the invention.

Capsules of the invention are suitable for various medical uses in humans. For instance, they can be used to reduce serum triglycerides, reduce serum cholesterol, reduce or prevent plaque formation, reduce or prevent platelet aggregation, treat or prevent atherosclerosis, treat or prevent cardiovascular disease, treat or prevent inflammatory diseases, treat auto-immune diseases, treat coronary heart disease, treat depression, treat Alzheimer's disease, treat attention deficit disorder, treat sickle cell disease, or treat metabolic syndrome. Thus a subject who received a medicament of the invention may have one of these conditions, or be in need of one of these effects.

In some embodiments, krill phospholipids are administered in a daily dose of from about 0.7 to about 3 grams.

MODES FOR CARRYING OUT THE INVENTION

Example 1: Krill Phospholipid Preparation

This example describes the extraction of oil from a wet material. A coagulum from krill comprising about 70% water, 15% lipids and about 15% other dry matter, mainly proteins, was obtained as described in reference 18. This material was subjected to an extraction procedure as follows. 3500 grams of pure ethanol was added to 1004 grams of the coagulum and stirred for 45 minutes. The mixture was then filtered through a filter paper applying vacuum on the receiving flask to obtain 3854 gram of filtrate. 1179 gram of the filtrate was subjected to evaporation on a rotary evaporator and the obtained dry matter was washed 4 times with a 60% solution of ethanol and finally the solvent was evaporated in a rotary evaporator. The obtained oil, 23.7 gram, was solid at room temperature and comprised 76.8% phospholipids. The content of EPA was 200 mg/gram and the content of DHA 87 mg/gram oil.

Example 2: Krill Phospholipid Preparation with Higher Purity

This example describes an alternative method for extraction of oil from the krill wet material, starting from a frozen paste from krill, which was subjected to an extraction procedure as described below. Unlike example 1, all steps were performed under a nitrogen atmosphere.

A frozen krill paste was subjected to an extraction procedure under a nitrogen atmosphere. The paste comprises about 65% water (assessed via dry matter), 17% lipids (about equal weights of phospholipids and neutral lipids), and about 18% other dry matter, mainly proteins.

100 kg of the frozen coagulum (−20° C.) was added to a vessel. Based on the water content of the coagulum, 350 kg of pure ethanol (99.8% w/w, room temp) was then added to the vessel, giving a final ethanol concentration in the liquid phase of about 84% w/w (~350 kg ethanol in 415 kg liquid solvents).

The mixture was stirred in the vessel for 45 minutes, with gentle heating if required. Four final temperatures were studied in separate batches, namely a) 2° C., b) 10° C., c) 15° C. and d) 20° C. After stirring was complete, the mixtures were allowed to settle, and they each included a red-coloured liquid phase and a wet slurry containing shell fragments and other insoluble materials. To remove the liquid phase from the slurry the mixtures were decanted, and the liquid material was put through a coarse filter and then serial-filtered through a 75 µm and 5 µm cartridge filter to obtain a) 345 kg, b) 366 kg, c) 372 kg or d) 374 kg of filtrate, with residual material remaining in the filtration cake.

The filtrates were then subjected to a sequence of washes. Firstly, de-ionized water was added to give ~60% w/w ethanol solutions (a: 137 kg water; b: 149 kg; c: 152 kg; d: 155 kg) and the mixtures were stirred for 10-15 minutes and left to settle for 12-24 hrs at room temperature (15-20° C.) in vessels having a valve at the base. The bottom phase was isolated by draining the bottom phase through the valve, to give between 5.4-9.0 kg of a lipid-rich fraction. The lipid-rich fraction was re-washed 2 to 5 times with 60% w/w ethanol at room temperature to give a final material which contained about 80% by weight phospholipids and 20% neutral lipids. In even the first wash, 85% of TMAO was removed, and the further washes led to material with undetectable TMAO (less than 1 mg N/100 g i.e. at least 20-fold lower than reported in Table X of reference 20).

This lipid-rich material was treated by cold acetone precipitation. Three parts w/w acetone were added and the lipid rich material was dissolved by gentle heating and slow stirring. The stirring was stopped and the mixture was cooled to 4° C. for precipitation. When the precipitation was complete, the upper solvent phase was removed. This cold precipitation procedure was performed three times in total, after first re-dissolving in fresh acetone each time.

The precipitate was then subjected to evaporation and freeze-drying to remove residual acetone and water. Batch c (i.e. extracted at 15° C., then washed 3×60% EtOH before cold acetone precipitation) provided 1.9 kg of solid material (an orange wax) consisting of 98% phospholipids/1.7% neutral lipids with a water content of 3%. Astaxanthins were present at <2 mg/kg. Amino acids, TMAO and homarine were all below the limit of quantification by standard analytical methods.

Looking at specific fatty acids, proportions were as follows, measured across several batches:

|  | C14:0 | C16:0 | 16/14 Ratio | C18:3 n-3 | C18:4 n-3 | 18:4/18:3 Ratio |
|---|---|---|---|---|---|---|
| Wet paste | 6-10% | 15-17% | 2-2.5 | 1.4-3.1% | 3.5-7% | 2-3 |
| Final material | 1.0-1.5% | 15-17% | 12-16 | 1.0-2.5% | 1.0-2.5% | 1-1.5 |

The purified phospholipids included both ether-linked and ester-linked fatty acids, but 10% or fewer were ether-linked. NMR showed ether-linked fatty acid moieties at position sn1 but not at sn2, and ether-linked fatty acids were either fully saturated or were monounsaturated. Where a phospholipid was a phosphatidylcholine, about 10% of the molecules included ether-linked fatty acids; where a phospholipid was a phosphatidylethanolamine (with or without N-acetylation), about 40% of the molecules included ether-linked fatty acids. PUFAs were seen only with ester linkages. 30-40% by weight of fatty acids in the purified phospholipids were omega-3, and these were distributed at the sn1 and sn2 positions (mainly at sn2). Most of the omega-3 fatty acids were EPA and/or DHA, with about 2× more EPA than DHA.

The lysophosphatidylcholine content (0.2-0.4 mol %) is very low in the purified phospholipids, when compared to the amount in the starting wet material (about 1.2-1.4 mol %). No molecules were detected where fatty acid chains had been lost at both the sn1 and sn2 positions. Lyso-phosphatidylethanolamine (with or without N-acetylation) and lyso-phosphatidylinositol also were not seen.

Thus the krill phospholipids obtained by this method have a high purity and a low level of specific contaminants. They are thus well-suited to pharmaceutical use, but their physical state (waxy solid, with a high viscosity even when warmed to 70° C.) is inconvenient for pharmaceutical preparation.

Example 3: Liquefaction of Purified Phospholipids

The material purified according to example 2 (or similar methods) is very viscous and sticky, which makes it unsuitable for filling into capsules. Thus purified krill phospholipids were thus combined with various hydrophilic and lipophilic additives as viscosity regulating agent:

| Hydrophilic additives | Lipophilic additives |
|---|---|
| Ethanol | Medium-chain triglycerides |
| Glycerol | Castor oil |
| Propylene glycol | Sesame oil |
| PEG 300 | Glyceryl Trioctanoate |
| PEG 400 | |

In early experiments, purified krill phospholipids (98% purity—see example 2) were mixed with MCTs and fully evaporated. The mixture was dissolved in excess ethanol and excess ethanol was removed by rotary evaporation. Results were as follows, where %s are expressed by weight:

| | Krill PLs (dry mass) (%) | MCT (%) | EtOH (%) | Result |
|---|---|---|---|---|
| Test 1 | 88.52 | 8.85 | 2.63 | Fine viscosity |
| Test 2 | 91.34 | 4.69 | 3.97 | Slightly higher than Test 1 |
| Test 3 | 89.26 | 8.92 | 1.8 | Too viscous for easy handling |
| Test 4 | 89.37 | 8.94 | 2.48 | Too viscous for easy handling |

Based on these results, 19 further compositions were designed and evaluated for viscosity using a variety of different viscosity-reducing agents. Viscosity was measured at both 25° C. and 40° C., using a shear rate of 100 s$^{-1}$ using an AG-G2 Rheometer with 40 mm plate/plate and 500 μm gap. Viscosity measurements were as follows, along with an observation whether the compositions remained homogeneous:

| Sample # | KPL (wt %) | Viscosity-reducing agent (wt %) | | Ethanol (wt %) | Temperature | Viscosity (Pa · s) | Homogeneous |
|---|---|---|---|---|---|---|---|
| 1 | 82.9 | MCT | 9.3 | 7.8 | 25° C. | 3 | No |
|   | 82.9 |     | 9.3 | 7.8 | 40° C. | 3 | No |
| 2 | 85.5 | MCT | 9.6 | 4.9 | 25° C. | 12 | No |
|   | 85.5 |     | 9.6 | 4.9 | 40° C. | 7 | No |
| 3 | 89.1 | MCT | 4.7 | 6.2 | 25° C. | 7 | No |
|   | 89.1 |     | 4.7 | 6.2 | 40° C. | 2 | No |
| 4 | 90.8 | MCT | 5.1 | 4.1 | 25° C. | 52 | No |
|   | 90.8 |     | 5.1 | 4.1 | 40° C. | 5 | No |
| 5 | 85.6 | MCT | 12.9 | 1.5 | 25° C. | 31 | No |
|   | 85.6 |     | 12.9 | 1.5 | 40° C. | 5 | No |
| 6 | 92.3 | None | 0.0 | 7.7 | 25° C. | 4 | Yes |
|   | 92.3 |      | 0.0 | 7.7 | 40° C. | 6 | Yes |
| 7 | 83.6 | MCT | 12.8 | 3.7 | 25° C. | 7 | No |
|   | 83.6 |     | 12.8 | 3.7 | 40° C. | 12 | No |
| 8 | 84.2 | Castor oil | 8.5 | 7.3 | 25° C. | 3 | No |
|   | 84.2 |            | 8.5 | 7.3 | 40° C. | 2 | No |
| 9 | 88.1 | Castor oil | 8.8 | 3.1 | 25° C. | 8 | No |
|   | 88.1 |            | 8.8 | 3.1 | 40° C. | 6 | No |
| 10 | 85.5 | Glyceryl Trioctanoate | 8.6 | 6.0 | 25° C. | 4 | No |
|    | 85.5 |                       | 8.6 | 6.0 | 40° C. | 5 | No |
| 11 | 83.1 | Glyceryl Trioctanoate | 8.3 | 8.6 | 25° C. | 1 | No |
|    | 83.1 |                       | 8.3 | 8.6 | 40° C. | 3 | No |
| 12 | 86.2 | Sesame oil | 8.8 | 5.0 | 25° C. | 4 | No |
|    | 86.2 |            | 8.8 | 5.0 | 40° C. | 11 | No |
| 13 | 83.5 | Sesame oil | 8.5 | 8.0 | 25° C. | 3 | No |
|    | 83.5 |            | 8.5 | 8.0 | 40° C. | 4 | No |
| 14 | 81.3 | Glycerol | 8.2 | 10.5 | 25° C. | 2 | Yes |
|    | 81.3 |          | 8.2 | 10.5 | 40° C. | 2 | Yes |
| 15 | 85.1 | Glycerol | 8.5 | 6.5 | 25° C. | 10 | Yes |
|    | 85.1 |          | 8.5 | 6.5 | 40° C. | 8 | Yes |
| 16 | 85.2 | Propylene glycol | 8.7 | 6.1 | 25° C. | 2 | Yes |
|    | 85.2 |                  | 8.7 | 6.1 | 40° C. | 2 | Yes |
| 17 | 89.0 | Propylene glycol | 8.9 | 2.0 | 25° C. | 7 | Yes |
|    | 89.0 |                  | 8.9 | 2.0 | 40° C. | 4 | Yes |
| 18 | 84.5 | PEG 300 | 8.5 | 7.0 | 25° C. | 2 | Yes |
|    | 84.5 |         | 8.5 | 7.0 | 40° C. | 1 | Yes |
| 19 | 89.2 | PEG 300 | 9.1 | 1.8 | 25° C. | 12 | Yes |
|    | 89.2 |         | 9.1 | 1.8 | 40° C. | 4 | Yes |

Thus, for instance, composition 16 has a suitable viscosity for convenient liquid processing and has a phospholipid concentration of 835 mg/mL, thus permitting a 700 mg dose to be achieved using a volume of around 840 μL, which will fit inside a size 00 hard capsule or a 14 minim soft capsule.

Further test compositions were prepared using ≥80% by weight of the purified phospholipids and a variety of viscosity-reducing agents using ethanol and one further component. The appearance and viscosity of these compositions was evaluated visually at room temperature. The following compositions have been prepared (%s are by weight):

| | Krill PL | Viscosity-reducing agent | EtOH | Visual result |
|---|---|---|---|---|
| Test 5 | 80 | Sesame oil | 15 | 5 | Homogenous. Viscous but flows OK. |
| Test 6 | 80 | Soybean oil | 15 | 5 | Homogenous. Viscous but flows OK. |
| Test 7 | 80 | Propylene glycol | 15 | 5 | Flows nicely, but a few lumps were observed indicating inhomogeneity. |
| Test 8 | 80 | PEG 300 | 15 | 5 | Homogenous, very good flow. |
| Test 9 | 80 | PEG 400 | 15 | 5 | Homogenous, very good flow (even better than Test 8). |
| Test 10 | 85 | PEG 400 | 15 | 0 | Homogenous but very viscous. |
| Test 11 | 85 | PEG 400 | 12.5 | 2.5 | Homogenous. Flows OK. |
| Test 12 | 90 | PEG 400 | 7.5 | 2.5 | Homogenous but extremely viscous. |
| Test 13 | 87 | PEG 400 | 10.5 | 2.5 | Homogenous. Flows OK. |

Further viscosity-reducing agents were tested as follows:

| | Krill PL | EtOH | PEG400 | PEG600 | MCT | Glycerol | Viscosity (Pa · s) 25° C. | 30° C. |
|---|---|---|---|---|---|---|---|---|
| Test 14 | 82.5 | 5 | 12.5 | — | — | — | 2987 | 1848 |
| Test 15 | 82.5 | 5 | — | — | 12.5 | — | 4229 | 3345 |
| Test 16 | 80 | 7.5 | 7.5 | — | — | 5 | 1595 | — |
| Test 17 | 80 | 7.5 | — | 7.5 | — | 5 | 737 | — |
| Test 18 | 82.5 | 5 | — | 12.5 | — | — | 2271 | 1708 |

All five of these were clear and homogenous, although 'Test 15' was not as stable as the others.

In these test compositions, the concentration of phospholipids in the liquid materials comfortably exceeded 680 mg/mL, and generally fell within the range of about 720-850 mg/mL. Thus with a capsule size above 16 minims it is straightforward to achieve a per-capsule dose of >700 mg.

Example 4: Encapsulation Studies

Krill phospholipids of ~98% purity (example 2) were formulated according to the 'Test 9' viscosity-reducing agent, whereas a krill extract with ~80% phospholipids purity (example 1) was formulated like the 'Test 11' viscosity-reducing agent. The flow properties of these liquid materials were suitable for filling into oral capsules (viscosity at 30° C. was 1270 mPa·s for the 98% purity material, and 1870 mPa·s for the 80% purity material), so it was encapsulated into soft gelatin capsules which included both glycerol and sorbitol as plasticisers. Stability was assessed over a 12 week period, with stability parameters including the amount in the capsule contents of phosphatidylcholine, lysophosphatidylcholine, ethanol, water, glycerol, and sorbitol. Results at the start of the study and after 12 weeks at 40° C. were as follows:

| Parameter | 80% purity | | 98% purity | |
|---|---|---|---|---|
| | Time zero | 12 weeks | Time zero | 12 weeks |
| PC content | 59.4% | 58.7% | 70.4% | 70.4% |
| LPC content | 0.42% | 1.09% | 0.25% | 0.99% |
| EtOH content | 1.3% | 1.4% | 3.7% | 3.5% |
| $H_2O$ content | 3.8% | 4.2% | 5.2% | 5.3% |
| Glycerol content | 2.8% | 6.5% | 3.8% | 7.8% |
| Sorbitol content | 0.3% | 0.8% | 0.4% | 1.0% |

Therefore the phospholipids were stable in the capsules, with very low levels of lyso-PC breakdown products being seen even after 12 weeks at 40° C. It was clear, however, that components from the capsule material (water, sorbitol, and particularly glycerol) were entering the contents. The liquid material which was used to fill the capsules contained no glycerol or sorbitol, and ≤1.2% water.

One way to inhibit migration of glycerol from the capsule into the contents is to include glycerol already within the liquid contents, as part of the viscosity-reducing agent.

Ethanol levels at time zero were 1.3% or 3.7%, whereas in the initial phospholipid mixture which was used to fill the capsules the level was 2.5% or 5%, respectively. Thus from 25-50% of the ethanol escaped from the capsules between filling and the beginning of the stability study i.e. during drying and storage. This loss of solvent is accompanied by an increase in viscosity of the contents.

It will be understood that the invention is described above by way of example only and modifications may be made while remaining within the scope and spirit of the invention.

REFERENCES

[1] Batetta B et al. (2009) *J Nutr* 139:1495-1501.
[2] WO2010/035013.
[3] CN-102987382-A.
[4] WO2012/172411.
[5] WO2013/127727.
[6] *Guidance for Industry—Size, Shape, and Other Physical Attributes of Generic Tablets and Capsules*—U.S. Department of Health and Human Services, Food and Drug Administration, Center for Drug Evaluation and Research (CDER), December 2013.
[7] *The Theory and Practice of Industrial Pharmacy*. Lachman et al. (3rd edition).
[8] WO2011/050474.
[9] Watanabe et al. (1991) *Nippon Suisan Gakkaishi* 57:681-94.
[10] WO 2014/207571.
[11] PCT/EP2015/050370
[12] Winther et al. (2011) *Lipids* 46:25-36.
[13] Bligh & Dyer (1959) *Can. J. Biochem. Physiol.* 37:911-917.
[14] Homan R et al. (1998) *J Chromatogr B Biomed Sci Appl* 708:21-26.
[15] Moreau et al. (2006) *Lipids* 41:727-734.
[16] US 2008/0058286.
[17] WO2009/027692.
[18] WO2008/117062.
[19] WO2010/097701.
[20] WO2013/102792.

The invention claimed is:

1. A pharmaceutically acceptable capsule including between 700-1200 mg krill phospholipids, wherein the capsule includes liquid contents comprising: (a) 80-95% by weight krill oil, wherein the krill oil includes 85% by weight or more of krill phospholipids; (b) from 2 to 10% of a lower alcohol selected from the group consisting of ethanol, 2-propanol, 1-propanol; and c) an additive selected from the group consisting of glycerol, propylene glycol, and polyethylene glycol.

2. The capsule of claim 1, which is a soft capsule.

3. The capsule of claim 1, wherein the krill phospholipids are a mixture of phospholipid compounds of formula (I) as defined herein:

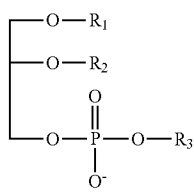

(I)

wherein $R_1$ and $R_2$ are each independently selected from a fatty acid moiety of formula —$COC_nH_m$, a fatty acid moiety of formula —$CH_2C_nH_m$, and —H, n is an integer in the range of 11-24 and m=2(n−p)+1, where p is the number of double bonds in the fatty acid moiety, and $R_3$ is H or is selected from a choline, ethanolamine, N-acetylethanolamine, inositol and serine.

4. The capsule of claim 3, wherein the mixture of phospholipid compounds of formula (I): includes less than 300 μg astaxanthins per gram of phospholipid; comprises less than 0.01% by weight trimethylamine N-oxide; comprises less than 0.01% by weight homarine; includes less than 1% by weight water; and has less than about 0.03% by weight PUFA polymers.

5. The capsule of claim 3, wherein the mixture of phospholipid compounds of formula (I): includes at least 85% by weight of phospholipid compounds of formula (I); includes less than 300 μg astaxanthins per gram of phospholipid; includes less than 0.01% by weight trimethylamine N-oxide; and is free from chloroform and hexane.

6. The capsule of claim 5, wherein the mixture of phospholipid compounds of formula (I): includes less than 0.01% by weight homarine; includes less than 5% by weight water; and includes less than 5% by weight sphingomyelin.

7. The capsule of claim 6, wherein the mixture of phospholipid compounds of formula (I): includes C16:0 and C14:0 fatty acid moieties, wherein the weight ratio of C16:0/C14:0 fatty acid moieties in the mixture is between 10:1 and 18:1; includes C18:4 n−3/C18:3 n−3 fatty acid moieties, wherein the weight ratio of C18:4 n−3/C18:3 n−3 fatty acid moieties is between 1:1 and 3:2; less than 1% by weight free fatty acids; has less than 0.005% by weight trimethylamine; and is free from canthaxanthin and flavonoid.

* * * * *